United States Patent [19]

Fischer

[11] Patent Number: Plant 6,647

[45] Date of Patent: Mar. 7, 1989

[54] AFRICAN VIOLET PLANT NAMED MIDNIGHT RUFFLES

[76] Inventor: Arnold Fischer, Kahlendamm 22, 3000 Hannover 51, Fed. Rep. of Germany

[21] Appl. No.: 92,150

[22] Filed: Aug. 13, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A cultivar of African violet named Midnight Ruffles, characterized by its large single dark violet-blue flowers which have ruffled edges; dark green leaves, compact growth habit, and its floriferousness.

1 Drawing Sheet

1

The present invention comprises a new and distinct cultivar of African violet plant, botanically known as *Saintpaulia ionantha,* named Midnight Ruffles.

The new cultivar is a product of a planned breeding program carried out by applicant in Hannover, Federal Republic of Germany. The basic objective of the breeding program was to create a new African violet cultivar having large, dark violet-blue ruffled flowers, dark green ruffled foliage, and highly floriferous and compact growth habits.

The new cultivar was originated from a cross made by applicant in the controlled breeding program. Both the female (or seed) and the male (or pollen) parents were unknown and unnamed seedlings.

Midnight Ruffles was discovered and selected by applicant as a flowering plant within the progeny of the stated cross in a controlled environment in Hannover, Federal Republic of Germany. Asexual reproduction of the new cultivar by leaf cuttings, as performed by me at Hannover, Federal Republic of Germany, has demonstrated that the combination of characteristics as herein disclosed for the new cultivar are firmly fixed and retained through successive generations of asexual reproduction.

Midnight Ruffles has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Midnight Ruffles which in combination distinguish this African violet as a new and distinct cultivar:

(1) Large dark violet-blue single zygomorphic rotate flowers with ruffled margins and a diameter of 30–35 mm.

(2) Dark green, pubescent foliage, oval shaped with slightly ruffled sinuate margins, cordate base and a broadly acute apex.

(3) Compact rosette habit with flowers held erect on strong upright peduncles.

(4) Very floriferous with flowers continuing to open for many weeks after the onset of flowering.

(5) Suitable for production in 10 cm pots finishing in 9–13 weeks when started from a 2¼" plantlet.

2

The new cultivar is most similar to the cultivar Blue Bird, disclosed in U.S. Plant Pat. No. 4,934. Midnight Ruffles is principally distinguished from Blue Bird by its slightly ruffled foliage and its darker violet blue flower color.

The accompanying photographic drawing shows a typical specimen plant of the new cultivar. The photograph is in black and white, with a single flower being colored to accurately depict the true flower color designated below by color values.

In the following description, color references are made to the Royal Horticultural Society Colour Chart (RHS), except where general colors of ordinary significance are referred to. Color values were taken under fluorescent light conditions at approximately 10:15 a.m. in Parrish, Fla.

Botanical classification: *Saintpaulia ionantha,* Ramat., cv. Midnight Ruffles.

Parentage: Unknown.

Propagation: The new cultivar holds its distinguishing characteristics through successive propagations by leaf cuttings.

Plant: From 5 cm to 10 cm tall when grown in pots, and approximately 20 cm in diameter when fully grown. The growth rate is vigorous, and the general shape of the fully grown plant is round.

*Leaves.*—Quantity: abundant. Shape: Oval with sinuate margins. Diameter: Up to 8 cm for a mature leaf. Texture: Pubescent, glossy. Ribs and veins: Pinnate. Color (upper side): 147A. Color (under side): 186 A and B with light green midrib and veins. Petioles: 186 A and B.

*Flowers.*—Buds: Size: About 1 cm×1 cm. Shape: Round. Rate of opening: Normal. Sepals: Shape: Lanceolate. Color: Purplish-green. Phyllaries: 2, lanceolate. Color: Purplish-green. Calyx: Shape: Funnel. Size: about 12 mm in diameter. Aspect: Pubescent. Peduncle: Length: up to 8 cm. Character: Erect, rigid. Color: Purplish-green. Individual flowers: Number of petals: 5. Size: 30–35 mm in diameter and 10 mm deep. Shape: Cup shaped when bloom first opens, becoming flat as bloom matures. Color (upper side): 89 A. Color (under side): 89 D. Flowers fade slightly as they age. Flower color may vary somewhat depending upon the amount of light, fertilizer, temperature and other growing conditions. Borne: Cymose clusters on upright peduncles up to 8 cm long. Flowering habit: Flowers profusely and intermittently year round with blooms lasting 2–3 weeks after which petals dry up but do not drop. Finishes in 9–12 weeks when a 2¼" plantlet is placed in a 10 cm pot.

*Reproductive organs.*—Stamens: Stamens borne singly on one side of ovary. 2 anthers basifixed. Anthers: 2 mm×2 mm yellow. Filaments: 3 mm, white with dark blue streaks. Pollen color: Yellow. Pistels: Number: 1. Styles: 1, 5–7 mm long. Stigma: Sticky, white. Ovaries: Superior. Roots: Fibrous and fine.

Disease resistance: No African violet diseases observed to date.

I claim:

1. A new and distinct cultivar of African violet named Midnight Ruffles, as illustrated and described, and particularly characterized by its large single dark violet-blue flowers which have ruffled edges; dark green leaves, compact growth habit, and its floriferousness.

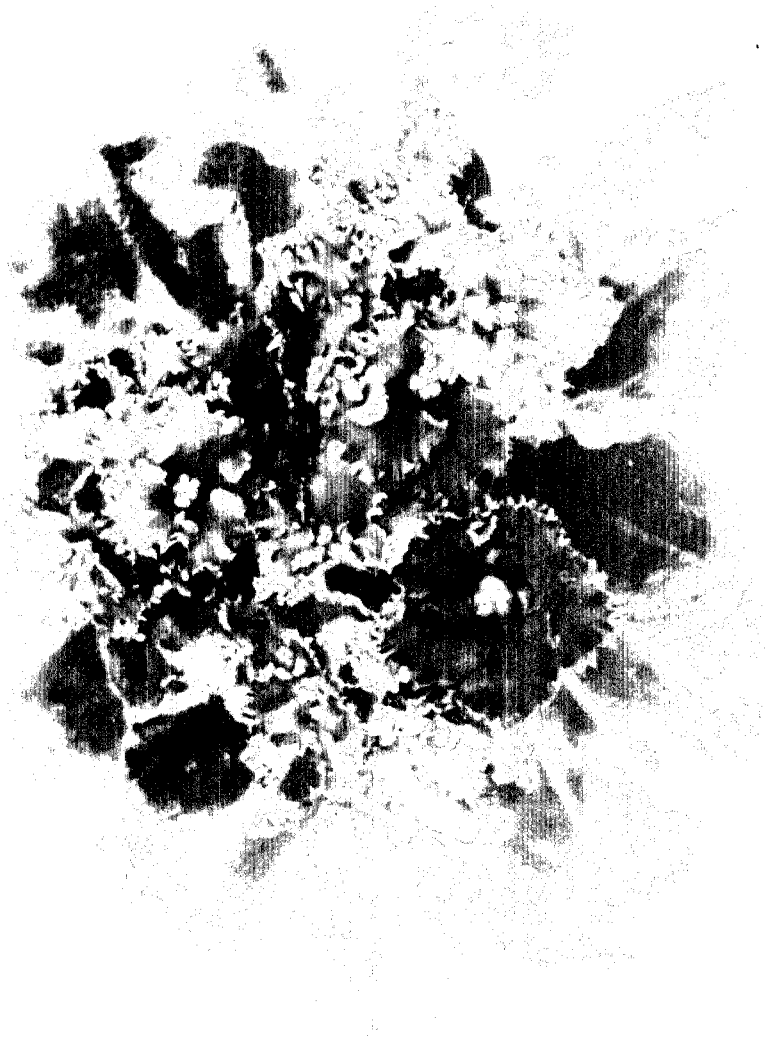

* * * * *